(12) United States Patent
Horvath et al.

(10) Patent No.: US 6,440,137 B1
(45) Date of Patent: Aug. 27, 2002

(54) MEDICAL FASTENER CAP SYSTEM

(76) Inventors: Andres A. Horvath, 4890 Crest Ave.; Fredric L. Williams, 3223 Algonquin La., both of Riverside, CA (US) 92503; Timothy Michael Williams, 7995 Magnolia Ave., #28E, Riverside, CA (US) 92504

( * ) Notice: Subject to any disclaimer, the term of this patent is extended or adjusted under 35 U.S.C. 154(b) by 0 days.

(21) Appl. No.: 09/838,452

(22) Filed: Apr. 18, 2001

Related U.S. Application Data

(60) Provisional application No. 60/197,701, filed on Apr. 18, 2000.

(51) Int. Cl.[7] .................................................. A61B 17/68
(52) U.S. Cl. ................................................. 606/73; 606/61
(58) Field of Search ................................ 606/60, 61, 72, 606/73; 411/396

(56) References Cited

U.S. PATENT DOCUMENTS

| | | | |
|---|---|---|---|
| 5,207,678 A | | 5/1993 | Harms et al. |
| 5,261,912 A | * | 11/1993 | Frigg .................... 606/61 |
| 5,536,268 A | * | 7/1996 | Griss .................... 606/61 |
| 5,667,508 A | * | 9/1997 | Errico et al. ............ 606/73 |
| 5,752,957 A | * | 5/1998 | Ralph et al. ............ 606/61 |
| 5,782,833 A | | 7/1998 | Haider |
| 5,810,818 A | * | 9/1998 | Errico et al. ............ 606/61 |
| 5,882,350 A | * | 3/1999 | Ralph et al. ............ 606/61 |
| 5,910,142 A | | 6/1999 | Tatar |
| 5,989,254 A | | 11/1999 | Katz |

* cited by examiner

Primary Examiner—Jeffrey A. Smith
(74) Attorney, Agent, or Firm—Gene Scott; Patent Law & Venture Group

(57) ABSTRACT

A fastening apparatus provides a fastener body with a female threaded cap receiver having a transverse groove for insertion of a rod. A fastener cap provides a disk shaped cap head and, a male threaded portion within a spaced apart concentric cylindrical rim. The cap head provides a tool engaging fixture to allow the fastener cap to be engaged with the fastener body so as to clamp the rod between the fastener body and the fastener cap. The cylindrical rim engages the cap receiver so as to prevent splaying.

3 Claims, 2 Drawing Sheets

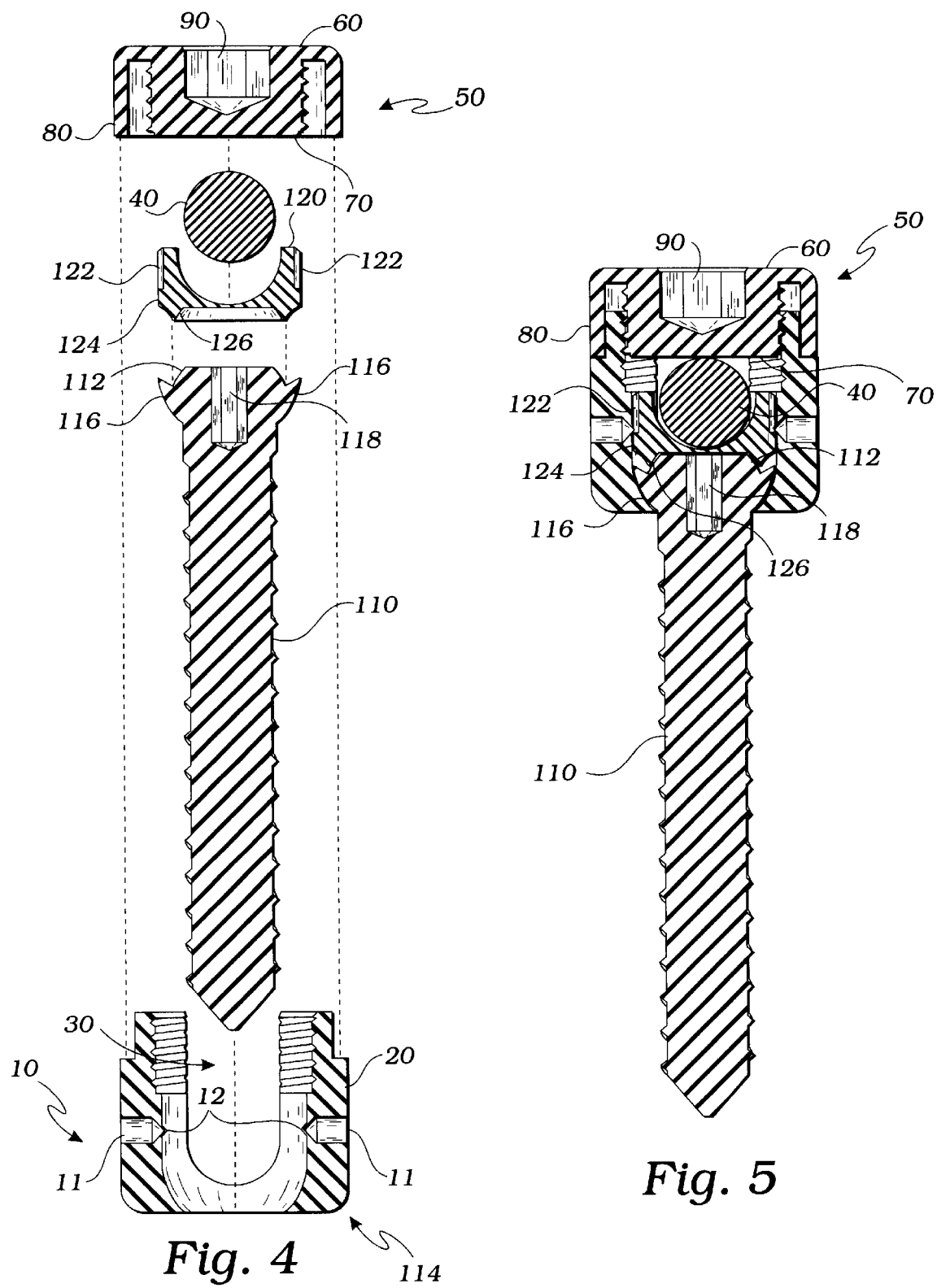

MEDICAL FASTENER CAP SYSTEM

The present invention claims the priority date of a prior filed provisional patent application having Ser. No. 60/197,701 and an official filing date of Apr. 18, 2000 and which discloses substantially the same invention as described herein.

BACKGROUND OF THE INVENTION

1. Field of the Invention

This invention relates generally to hardware fasteners and more particularly to plural fasteners all having a common fastener head and cap system.

2. Description of Related Art

The following art defines the present state of this field:

Harms et al., U.S. Pat. No. 5,207,678 describes a receiver member for a pedicle screw which provides for hingedly connecting a screw comprising a threaded shaft portion and a sphericalsegment-shaped head on the one hand and a rod on the other hand. In order to improve the stocking costs for screws of different shaft lengths and shaft diameters, the receiver member has a receiver chamber therein, the receiver chamber has a bore at one end thereof for passing the threaded shaft portion followed by an inner hollow spherical-segment-shaped portion for supporting the head of the screw to be received, and an aperture on the side opposite to the bore for inserting the screw. Further, a compression member is provided which exerts, in assembled state, a force onto the head such that the head is pressed against the hollow spherical-segment-shaped portion. The new receiver member provides that only screws with different screw shafts must be stocked and in operation these screws can be then assembled with the uniform receiver members.

Haider U.S. Pat No. 5,782,833 describes a pedicle screw assembly for use with a rod for the immobilization of bone segments. The assembly is composed of a screw, a polyaxial housing, a washer, a set screw, and a cup-shaped cap. When the screw is placed inside the polyaxial housing, the head of the screw comes into contact with a middle section of the polyaxial housing and is secured into the bone so that the polyaxial housing is pivotable with three degrees of freedom. The housing includes a pair of upstanding posts with interior threads. A washer is inserted between the head of the screw and the rod. A cap, having a bottom, with a pair of posts accommodating openings and a lateral cross connector, is placed over the posts so that the cross connection engages the rod. A set screw is threaded into the housing posts to secure the rod within the housing.

Tatar, U.S. Pat. No. 5,910,142 describes a polyaxial pedicle screw device for use with rod implant apparatus, which utilizes a rod mounted ferrule, including a screw having a curvate head and a rod receiving body. The body has a rod receiving channel and an axial bore into which the head of the screw is inserted. The interior surface of the bore is inwardly curvate at the lower end thereof to form a socket for polyaxially retaining the curvate head of the screw. In an initial position the screw head remains polyaxially free with respect to the body. The rod mounted ferrule seats into a small curvate recess in the upper portion of the screw head such that the rod may enter the body at a variety of angles while maintaining a secure seating against the head of the screw. The insertion of a top set screw compresses down on the ferrule, locking the rod in position, and onto the screw head, locking it and the body in position, thus completely securing the assembly.

Katz, U.S. Pat No. 5,989,254 describes a pedicle screw assembly consisting of a screw having a part spherical head providing a saddle shaped contact surface for a connecting rod, the head being held in a coupling member allowing limited angular movement between the screw and coupling member in one plane only and this plane is at right angles to the contact surface. Surfaces are provided in the connecting member for supporting a connecting rod, which is securable in the coupling member by a cap engaging in the coupling member to clamp the connecting rod against the supporting surfaces while still enabling the screw to move angularly with respect to the coupling member.

The prior art teaches the use of bone tissue engaged fasteners but does not teach a fastener with a cap having tubular rim for preventing a rod clamping portion of the fastener to be deformed by action of the rod. The present invention fulfills these needs and provides further related advantages as described in the following summary.

SUMMARY OF THE INVENTION

The present invention teaches certain benefits in construction and use which give rise to the objectives described below.

A fastening apparatus provides a fastener body with a female threaded cap receiver having a transverse groove for insertion of a rod. A fastener cap provides a disk shaped cap head and, a male threaded portion within a spaced apart concentric cylindrical rim. The cap head provides a tool engaging fixture to allow the fastener cap to be engaged with the fastener body so as to clamp the rod between the fastener body and the fastener cap. The cylindrical rim engages the cap receiver so as to prevent splaying.

A primary objective of the present invention is to provide an apparatus and method of use of such apparatus that provides advantages not taught by the prior art.

Another objective is to provide such an invention capable of angular shaft rotation and positioning.

A further objective is to provide such an invention capable of capturing a washer within the fastener body.

A still further objective is to provide such an invention capable of securing a fastener interconnecting shaft without splaying of the fastener body elements.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 4 is an exploded view of the embodiment of FIG. 2 shown in section; and

FIG. 5 is a section view thereof shown as assembled.

DETAILED DESCRIPTION OF THE INVENTION

The above described drawing figures illustrate the invention in at least one of its preferred embodiments, which is further defined in detail in the following description.

Figure 1:
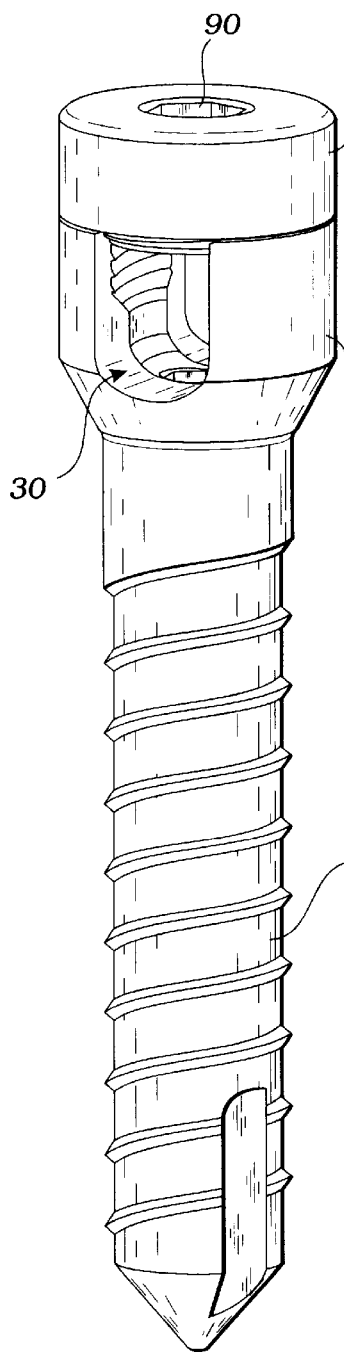
FIGS. 1–3 are perspective views of preferred embodiments of the invention.

The invention is a fastening apparatus designed for threaded insertion into bone tissue and is therefore made of a titanium alloy compatible with human physiology. It has a fastener body 10, shown in FIG. 1, providing a female threaded cap receiving means 20 and a transverse groove 30 for receiving a rod 40. The rod 40 is not a part of the present invention but is used to interconnect plural units of the fastening apparatus. A fastener cap 50 provides a disk shaped cap head 60 and, depending from it, and integral with it, a male threaded portion 70 within a spaced apart concentric cylindrical rim 80. The cap head 60 provides a tool engaging means 90, such as a hex depression commonly used to accept an Allen wrench for turning the fastener cap 50 onto the fastener body 10 for clamping the rod 40 in place. The cylindrical rim 80 engages the cap receiving means 20 to prevent splaying of the cap receiving means 20. This is an important aspect of the present invention and provides superior results as compared to the prior art described above.

Figure 2:
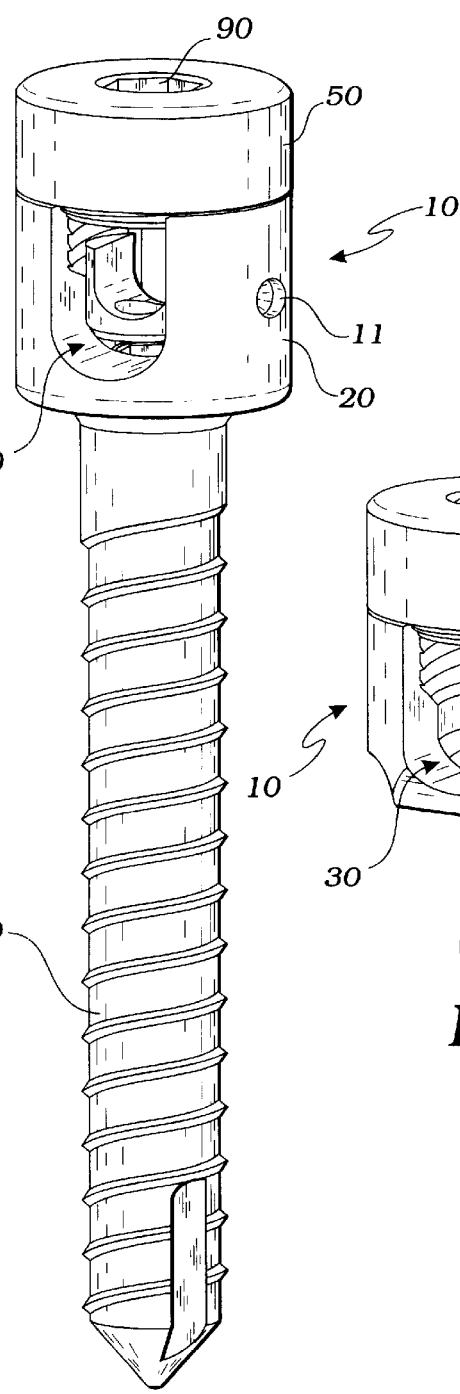
Figure 3:
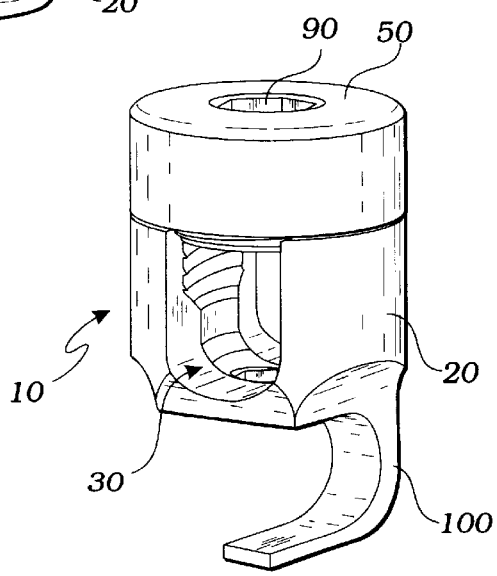

Preferably, the fastener body 10 further provides a hook shaped finger 100 or a male threaded shaft 110 depending therefrom, as shown in FIGS. 3 and 2 respectively. These features provide a way for the fastener body 10 and cap 50 to be mounted to, or within, bone structures of the body.

The male threaded shaft 110 and the fastener body 10 may be cooperatively engaged for pivotal movement of the threaded shaft 110 within the fastener body 10. This is clearly shown in FIG. 5. A washer 120 is used to advantage in this fastener system. The washer 120 has a generally U-shaped conformation with plural opposing grooves 122 formed on an outside wall 124 of the washer 120. The fastener body 10 provides inwardly protruding upsets 120 positioned for engaging the opposing grooves 122 so as to capture the washer 120 within the fastener body 10. The manner in which this is accomplished is as follows. The washer 120 is inserted into the fastener body 10, as is clearly shown in FIG. 2, and aligned with the transverse groove 30. Next, a center punch or similar tool (not shown) is inserted into each one of a pair of opposing blind holes 11 in the fastener body 10 as shown. These holes 11 terminate within 0.002 inches of the interior of the fastener body 10. The center punch is used to deform the material at the bottom of the holes 11 to form the upsets 12, forcing this material to protrude into the interior of the fastener body 10 and thus into the opposing grooves 122.

The washer 120 further provides a spherical annular surface 126 adapted by size and shape for engaging a spherical surface 112 at a proximal end 114 of the threaded shaft 110 whereby the spherical surface 112 of the threaded shaft 110 and the spherical annular surface 126 of the washer 120 are able to move in rotational communion with surfaces 112 and 126 in contact. The spherical surface 112 at the proximal end 114 of the threaded shaft 110 terminates at a circular raised peripheral lip 116. This construction enables the rotation of the threaded shaft 110 over a total angular excursion of at least 40 degrees and yet remain in structurally sound interconnection with the washer 120. Preferably, a hex shaped recess 118 is formed in the proximal end 114 of threaded shaft 110 for enabling the shaft 110 to be driven by an Allen wrench.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A fastening apparatus which comprises: a fastener body providing a threaded cap receiving means, and a transverse groove for receiving a rod, and a threaded shaft depending therefrom, and engaged therewith, a fastener cap providing a disk shaped cap head and, depending therefrom and integral therewith, a threaded portion within a spaced apart concentric cylindrical rim; the cap head providing a tool engaging means; the cylindrical rim engaging the cap receiving means to prevent splaying thereof; and a washer having plural opposing grooves therein, the fastener body providing inwardly protruding upsets engaging the opposing grooves so as to capture the washer within the fastener body.

2. The apparatus of claim 1 wherein the washer provides a spherical annular surface engaging a spherical surface at a proximal end of the threaded shaft whereby the spherical surface of the threaded shaft and the spherical annular surface of the washer are in rotational communion.

3. The apparatus of claim 2 wherein the spherical surface at the proximal end of the threaded shaft terminates at a circular raised peripheral lip.

* * * * *